(12) United States Patent
Li et al.

(10) Patent No.: US 11,998,397 B2
(45) Date of Patent: *Jun. 4, 2024

(54) THERMAL CONDUCTIVE LAYER FOR TRANSDUCER FACE TEMPERATURE REDUCTION

(71) Applicant: FUJIFILM SONOSITE, INC., Bothell, WA (US)

(72) Inventors: Wei Li, Bothell, WA (US); Keith Williams, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,645

(22) Filed: Feb. 9, 2023

(65) Prior Publication Data

US 2023/0181167 A1 Jun. 15, 2023

Related U.S. Application Data

(63) Continuation of application No. 16/226,415, filed on Dec. 19, 2018, now Pat. No. 11,583,259.

(51) Int. Cl.
*A61B 8/00* (2006.01)
*B06B 1/06* (2006.01)

(52) U.S. Cl.
CPC ............ *A61B 8/546* (2013.01); *A61B 8/4245* (2013.01); *A61B 8/4444* (2013.01); *A61B 8/4494* (2013.01); *B06B 1/067* (2013.01); *A61B 2562/182* (2013.01)

(58) Field of Classification Search
CPC .............................. A61B 8/546; B06B 1/067
See application file for complete search history.

(56) References Cited

U.S. PATENT DOCUMENTS

| 5,973,927 A | 10/1999 | Tanaka | |
| 2006/0100513 A1* | 5/2006 | Hashimoto | G10K 11/004 600/437 |
| 2008/0009742 A1 | 1/2008 | Kondoh | |

(Continued)

FOREIGN PATENT DOCUMENTS

| EP | 1879024 A1 | 1/2008 |
| EP | 2992829 A1 | 3/2016 |

(Continued)

OTHER PUBLICATIONS

Extended European Search Report on the Patentabilty of Application No. 19900629.7 dated Jul. 15, 2022, 7 pages.

(Continued)

*Primary Examiner* — Colin T. Sakamoto
*Assistant Examiner* — Tommy T Ly
(74) *Attorney, Agent, or Firm* — Womble Bond Dickinson (US) LLP

(57) ABSTRACT

A method and apparatus are disclosed herein for a thermally conductive layer for transducer face temperature reduction in an ultrasound transducer assembly. In one embodiment, the ultrasound transducer assembly comprises: a transducer layer configured to emit ultrasound energy; one or more matching layers overlaying the transducer layer; a thermally conductive layer overlaying the one or more matching layers; and a lens overlaying the thermally conductive layer.

18 Claims, 6 Drawing Sheets

(56) References Cited

U.S. PATENT DOCUMENTS

| | | |
|---|---|---|
| 2009/0234233 A1 | 9/2009 | Nagano et al. |
| 2011/0193007 A1* | 8/2011 | Avakian .................. C08L 67/04 |
| | | 252/582 |
| 2012/0172721 A1* | 7/2012 | Curra .................... A61B 8/4494 |
| | | 600/447 |
| 2014/0375171 A1 | 12/2014 | Tai |
| 2015/0011889 A1 | 1/2015 | Lee |
| 2015/0115773 A1 | 4/2015 | Li et al. |
| 2015/0182999 A1* | 7/2015 | Zhao ..................... B06B 1/0622 |
| | | 310/334 |
| 2017/0164926 A1* | 6/2017 | Spicci .................. A61B 8/4281 |
| 2018/0062069 A1* | 3/2018 | Jin ......................... H10N 30/01 |
| 2018/0271372 A1 | 9/2018 | Lee et al. |
| 2018/0296195 A1 | 10/2018 | Okuda |
| 2019/0183459 A1* | 6/2019 | Sawada .................... G01K 7/42 |
| 2020/0345328 A1 | 11/2020 | Li et al. |
| 2020/0397406 A1 | 12/2020 | Spicci et al. |

FOREIGN PATENT DOCUMENTS

| | | |
|---|---|---|
| JP | 02-203846 A | 8/1990 |
| JP | 10-022326 A | 1/1998 |
| JP | 2001-074710 A | 3/2001 |
| JP | 2006-025892 A | 2/2006 |
| JP | 2017-099504 A | 6/2017 |
| JP | 2018-532307 A | 11/2018 |
| KR | 10-1195671 B1 | 10/2012 |
| WO | 2016/117721 A1 | 7/2016 |
| WO | 2018/178382 A1 | 10/2018 |

OTHER PUBLICATIONS

International Preliminary Report on Patentability received for PCT Patent Application No. PCT/US19/62891, dated Jul. 1, 2021, 11 pages.
International Search Report and Written Opinion received for PCT Patent Application No. PCT/US19/62891, dated Mar. 19, 2020, 12 pages.
Notice of Reasons for Refusal received for Japanese Patent Application No. 2021-534380, dated Mar. 28, 2023, 8 pages (4 pages of English Translation and 4 pages of Original Document).

* cited by examiner

THERMAL CONDUCTIVE LAYER FOR TRANSDUCER FACE TEMPERATURE REDUCTION

This application is a continuation of co-pending U.S. application Ser. No. 16/226,415, filed Dec. 19, 2018, which is hereby incorporated by this reference in its entirety.

FIELD OF THE INVENTION

The present invention relates generally to ultrasound transducer; more specifically, the present invention relates to ultrasound transducer assemblies that include at least one thermally conductive layer.

BACKGROUND OF THE INVENTION

Transducers, such as acoustic transducers, are used in medical imaging where an acoustic probe transmits and receives ultrasound waves to create images of the internal tissues of a patient. Generally, it is desirable to use the acoustic probe at a maximum permissible acoustic intensity to enable higher quality imaging, which may be achieved via better penetration of the acoustic waves into the patient's tissues. However, operating the acoustic probe at higher acoustic intensities may result in excessive heat being generated in the transducer assembly.

Limits exist on the maximum external temperature of an acoustic probe at points of contact with the patient. In certain modes of operation of the acoustic probe, the heat generated within the transducer elements or its assembly may cause the temperature of some regions of the probe surface to exceed permissible limits.

Transducer assemblies are generally fabricated employing materials with lower intrinsic thermal conductivity. Such transducer assemblies may result in the overheating of the probe. Disadvantageously, many previous attempts to enhance the thermal conductivity of the acoustic probe have had limited effect on the face temperature of the probe and therefore may be ineffective in sufficiently reducing the face temperature enough to prevent discomfort to a patient.

Thus, it is desirable to dissipate the heat that may be trapped in the array of transducer elements in order to circumvent the overheating of the patient contact surfaces of the transducer assembly.

SUMMARY OF THE INVENTION

A method and apparatus are disclosed herein for a thermally conductive layer for transducer face temperature reduction in an ultrasound transducer assembly. In one embodiment, the ultrasound transducer assembly comprises: a transducer layer configured to emit ultrasound energy; one or more matching layers overlaying the transducer layer; a thermally conductive layer overlaying the one or more matching layers; and a lens overlaying the thermally conductive layer.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

An ultrasound transducer assembly and method for fabricating the transducer array therein are disclosed. In one embodiment, the transducer array has a reduced face temperature. This is accomplished, at least in part, by including a thermally conductive layer overlaying or otherwise on top of the outer surface of one or more matching layers that overlays a transducer layer. In one embodiment, the thermally conductive layer (e.g., a gold layer, etc.) comprises a coating achieved through deposition. In one embodiment, the thermally conductive layer wraps around the outer sides of a backing layer holding the transducer array, where the layer can be thermally coupled to a shield. In one embodiment, the thermally conductive layer is also electrically conductive, such that the layer is both thermally and electrically coupled to the shield.

Figure 1:
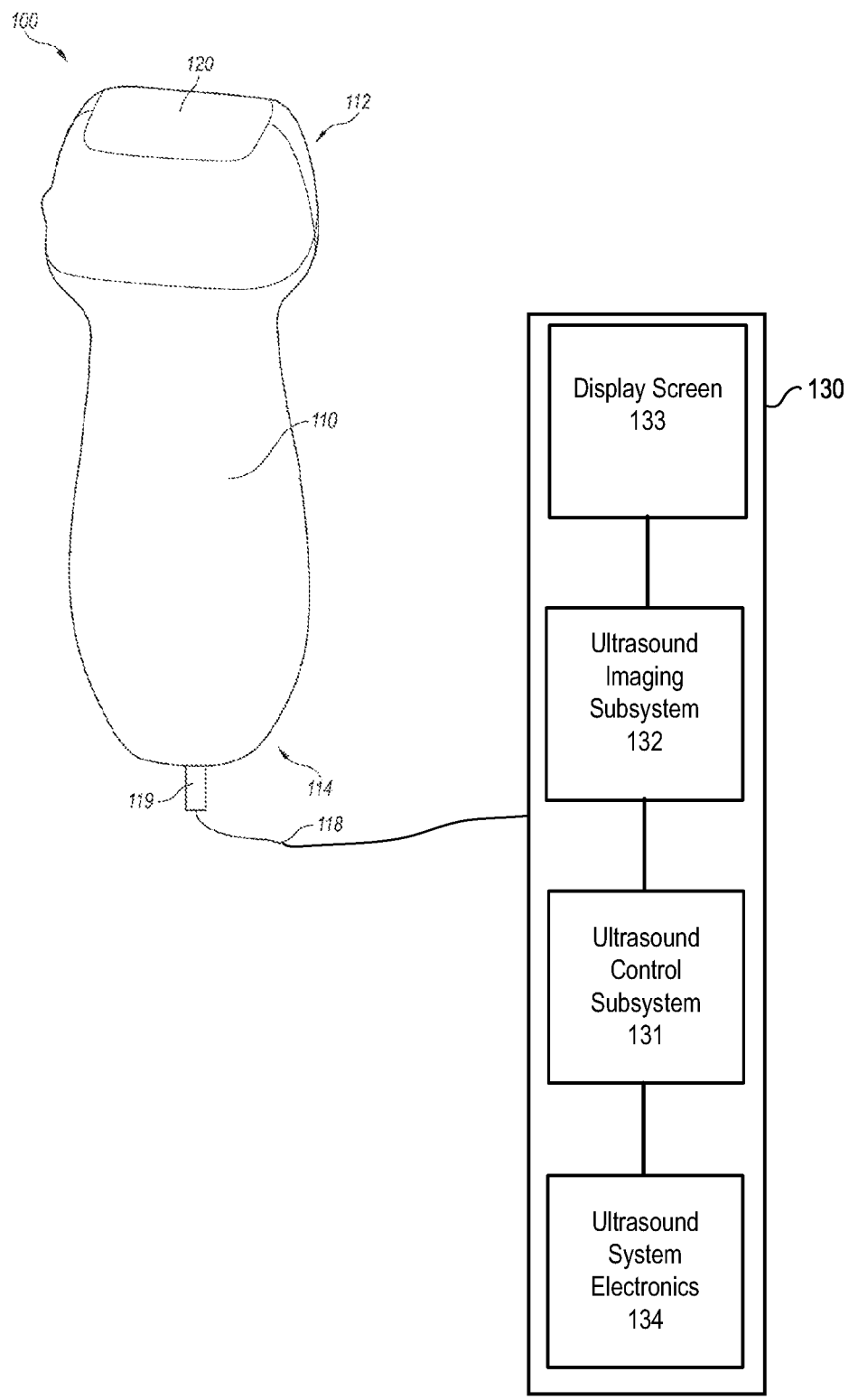
FIG. 1 illustrates one embodiment of an ultrasound transducer probe having an ultrasound transducer assembly.

FIG. 1 illustrates one embodiment of an ultrasound transducer probe having an ultrasound transducer assembly configured in accordance with an embodiment of the disclosed technology. Referring to FIG. 1, ultrasound transducer probe 100 includes an enclosure 110 extending between a distal end portion 112 and a proximal end portion 114. The ultrasound transducer probe 100 is electrically coupled to an ultrasound imaging system 130 via a cable 118 that is attached to the proximal end of the probe by a strain relief element 119.

A transducer assembly 120 having one or more transducer elements is electrically coupled to the system electronics. In operation, transducer assembly 120 transmits ultrasound energy from the one or more transducer elements toward a subject and receives ultrasound echoes from the subject. The ultrasound echoes are converted into electrical signals by the one or more transducer elements and electrically transmitted to the system electronics in ultrasound imaging system 130 to form one or more ultrasound images.

Capturing ultrasound data from a subject using an exemplary transducer assembly (e.g., the transducer assembly 120) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In one embodiment, ultrasound imaging system 130 includes ultrasound system electronics 134 that comprises one or more processors, integrated circuits, ASICs, FPGAs, and power sources to support the functioning of ultrasound imaging system 130 in a manner well-known in the art. In one embodiment, ultrasound imaging system 130 also includes ultrasound control subsystem 131 having one or more processors. At least one processor causes electrical signals to be sent to the transducer(s) of probe 100 to emit sound waves and also receives the electrical pulses from the probe that were created from the returning echoes. One or more processors processes the raw data associated with the received electrical pulses and forms an image that is sent to ultrasound imaging subsystem 132, which displays the image on display screen 133. Thus, display screen 133 displays ultrasound images from the ultrasound data processed by the processor of ultrasound control subsystem 131.

In one embodiment, the ultrasound system also has one or more user input devices (e.g., a keyboard, a cursor control device, etc.) that inputs data and allows the taking of measurements from the display of the ultrasound display subsystem, a disk storage device (e.g., hard, floppy, thumb drive, compact disks (CD), digital video discs (DVDs)) for storing the acquired images, and a printer that prints the image from the displayed data. These also have not been shown in FIG. 1 to avoid obscuring the techniques disclosed herein.

Figure 2A:
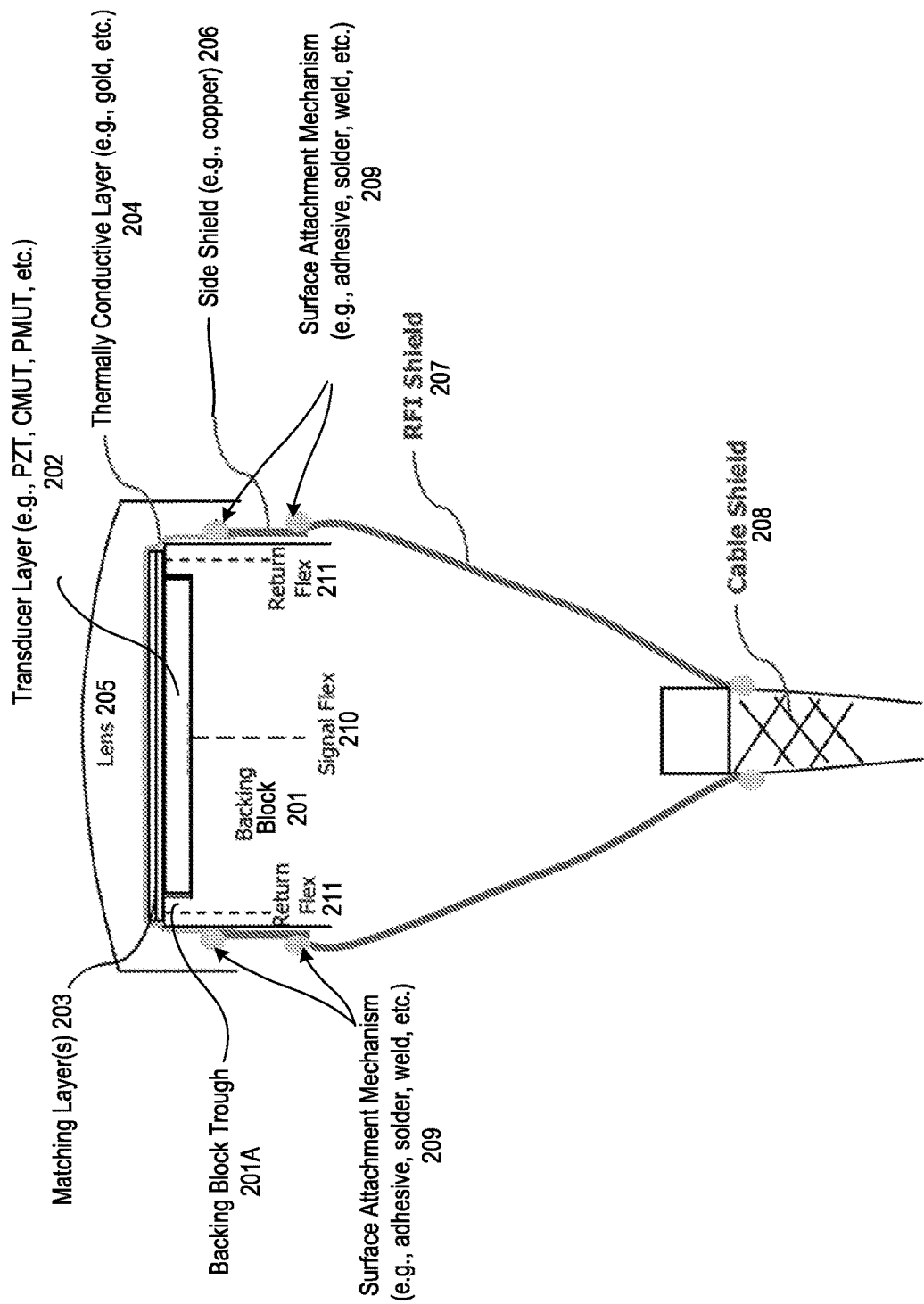
FIG. 2A illustrates a side section view of one embodiment of an ultrasound transducer assembly.

In one embodiment, the ultrasound transducer assembly comprises a transducer layer configured to emit ultrasound energy, one or more matching layers overlaying the transducer layer, a thermally conductive layer overlaying the one or more matching layers, and a lens overlaying the thermally conductive layer. FIG. 2A illustrates a side section view of one embodiment of an ultrasound transducer assembly.

Referring to FIG. 2A, in one embodiment, the ultrasound transducer assembly comprises a transducer layer (transducer) 202 disposed within a channel or trough 201A of a backing layer 201. In one embodiment, transducer layer 202 includes one or more transducer elements configured to emit ultrasound energy at some operating frequencies (e.g., between 1 MHz and about 50 MHz). In one embodiment, transducer layer 202 comprises a piezoelectric material (e.g., lead zirconate titanate (PZT)). Alternatively, transducer layer 202 comprises a piezoelectric micromachined ultrasound transducer (PMUT), a capacitive micromachined ultrasound transducer (CMUT), an electrostrictive ceramic material, or another suitable transducer material.

Backing layer 201 is configured to absorb and dissipate acoustic and thermal energy produced by transducer elements of transducer layer 202. In one embodiment, backing layer 201 comprises a loaded epoxy (e.g., an epoxy loaded with tungsten particles) and/or another suitable material having one or more plates (not shown) extending therethrough.

In one embodiment, a dematching layer (not shown) is positioned between transducer layer 202 and backing layer 201. In one embodiment, the dematching layer comprises a material that has acoustic impedance significantly different than an acoustic impedance of transducer layer 202, such as, for example, tungsten carbide (WC), which has an acoustic impedance significantly greater than the acoustic impedance of PZT. Alternatively, the dematching layer comprises aluminum nitride (AlN), polycrystalline silicon, copper loaded graphite, or another suitable dematching material.

A signal flex 210 carries electrical pulses from the ultrasound control system to transducer layer 202 in a manner well-known in the art. Note that only a portion of signal flex 210 is shown to avoid obscuring the present invention. Also, ground return flex 211 operates in a manner well-known in the art and is only partially shown as well.

One or more matching layers 203 overlay transducer layer 202 between transducer layer 202 and lens 205. In one embodiment, matching layers 203 are bonded to each other and to transducer layer 202 in a manner well-known in the art. In one embodiment, matching layers 203 of the transducer assembly includes three matching layers; in other embodiments, however, matching layers 203 of the transducer assembly includes two or fewer matching layers or four or more matching layers.

Thermally conductive layer 204 overlays matching layers 203. In one embodiment, thermally conductive layer 204 is between acoustic lens 205 and the top matching layer of matching layers 203. In one embodiment, acoustic lens 205 comprises an acoustically transparent material such as, for example, room temperature vulcanization silicone (RTV) or another suitable acoustic material.

In one embodiment, thermally conducive layer 204 is bonded or otherwise in thermal contact with the top surface of the top matching layer in matching layers 203 and lens 205.

Thermally conductive layer 204 reduces transducer face temperature. This is accomplished by transferring or otherwise dissipating thermal energy away from lens 205 and its surrounding area of the ultrasound transducer assembly.

In one embodiment, in order to reduce transducer face temperature, the material comprising thermally conductive layer 204 has a thermal conductivity greater than 100 W/m·K. In one embodiment, thermally conductive layer 204 comprises an electrically conductive material. In one embodiment, thermally conductive layer 204 comprises a metal, metal-alloy or non-metal but electrically-conductive material that has high thermal conductivity. Examples of such materials include, but are not limited to, gold, silver, copper, aluminum, magnesium, beryllium, brass, bronze, molybdenum, rhodium, tungsten, zinc, carbon (e.g., graphite, pyrolytic graphite, etc.). These materials have both thermal and EMI-shield benefits in their use as an overlaying material.

In one embodiment, thermally conductive layer 204 comprises non-electrically-conductive materials having high thermal conductivity. Examples of such materials include, but are not limited to, aluminum nitride, and alumina (aluminum oxide, $Al_2O_3$). In one embodiment, thermally conductive layer 204 is a combination of thermally and electrically conductive materials that are acoustically transparent. For example, in one embodiment, a thermally conductive layer is deposited on top of an electrically conductive layer to create thermally conductive layer 204. Alternatively, thermally conductive layer 204 is patterned or sectioned with thermally conductive and electrically conductive materials.

In one embodiment, thermally conductive layer 204 is a coating that is deposited over matching layers 203. For electrically-conductive materials mentioned above, in one embodiment, the coating is achieved through either direct-sputtering or electroplating (with maybe a very thin sputtered electrically-conductive seed-layer). For non-electrically-conductive materials mentioned above, the coating is achieved through direct-sputtering. Note that other deposition techniques may be used to deposit thermally conductive layer 204.

In one embodiment, thermally conductive layer 204 is bonded or otherwise attached to the top matching layer of matching layers 203. The bonding may be accomplished through the use of an adhesive.

In one embodiment, the thickness of thermally conductive layer 204 is dependent upon the frequency of the transducer layer 202. In one embodiment, thermally conductive layer 204 comprises a 3000 Angstrom gold layer that is coated over matching layers 203 via deposition for use in a 9 MHz probe. Gold of 3000 Angstrom thick at 9 MHz is acoustically transparent and inert in that it doesn't interfere with wet processing steps that may be used in creating the ultrasound transducer assembly after the gold deposition. Note that coating thicknesses other than 3000 Angstroms may be used. If the frequency is lower than, for example, 9 MHz, then the layer can be thicker because it would not impact performance.

Figure 3:
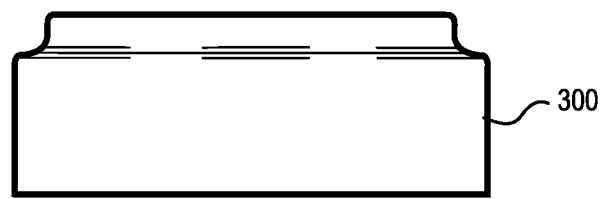
FIG. 3 illustrates an example of a thermally conductive layer that covers one or more matching layers and a transducer layer (which are not shown).

In one embodiment, thermally conductive layer 204 covers matching layers 203 and transducer layer 202. FIG. 3 illustrates an example of thermally conductive layer 300 that covers one or more matching layers and a transducer layer such as matching layers 203 and transducer layer 202 of FIG. 2A. Referring back to FIG. 2A, thermally conductive layer 204 extends down the sides of backing layer 201 so that it extends below a bottom plane of transducer layer 202 in backing layer 201.

In one embodiment, thermally conductive layer 204 extends to and is thermally coupled with an array side shield 206. In one embodiment, side shield 206 is wrapped around the transducer layer 202 and backing block 201 before lensing. In one embodiment, side shield 206 is a thermally conductive side shield comprising a thermally conductive material. Note that the material of side shield 206 is typically electrically conductive as well. In one embodiment, side shield 206 comprises copper, gold, silver, aluminum, magnesium, beryllium, brass, bronze, molybdenum, rhodium, tungsten, zinc.

In one embodiment, side shield 206 is thermally coupled with thermally conductive layer 204 at connection points, to form a thermally conductive path, using a surface attachment mechanism 209, such as, for example, an adhesive, solder, weld, etc. In one embodiment, the adhesive comprises glue, cement, mucilage, paste, or any substance applied to one surface, or both surfaces, of two separate items that binds them together and resists separation. In one embodiment, the surface attachment mechanism 209 comprises a thermally conductive material. Examples of thermally conductive material used to thermally couple side shield 206 to thermally conductive layer 204 include, but are not limited to, silver epoxy (e.g., silver epoxy paint, silver epoxy paste, silver epoxy beads, etc.), etc.). Note that other thermally conductive materials to thermally couple thermally conductive layer 204 to side shield 206 may be used.

In one embodiment, side shield 206 is electrically coupled with thermally conductive layer 204 at connection points to form an electrically conductive path as well as a thermally conductive path.

In one embodiment, the ultrasound transducer assembly comprises a radio-frequency interference (RFI) shield 207 thermally coupled to side shield 206. In one embodiment, RFI shield 207 is a shield wrapped around the array-flex-circuit and cable-printed-circuit-board (PCB) junction. This may occur after cabling.

In one embodiment, RFI shield 207 is thermally coupled with side shield 206 at connection points using a surface attachment mechanism, such as, for example, an adhesive, solder, weld, etc. In one embodiment, the surface attachment mechanism comprises a thermally conductive material. Examples of thermally conductive material used to thermally couple RFI shield 207 to side shield 206 include, but are not limited to, silver epoxy (e.g., silver epoxy paint, silver epoxy paste, silver epoxy beads, etc.), etc. Note that other thermally conductive materials to thermally couple side shield 206 to RFI shield 207 may be used.

In one embodiment, the ultrasound transducer assembly comprises a cable shield 208 that is coupled to RFI shield 207. In one embodiment, cable shield 208 includes a braid. In one embodiment, cable shield 208 is coupled to RFI shield 207 at connection points using a surface attachment mechanism, such as, for example, an adhesive (e.g., silver-epoxy), solder, weld, etc.

By thermally coupling thermally conductive layer 204 to side shield 206, thermally coupling side shield 206 to RFI shield 207 and thermally coupling RFI shield 207 to cable shield 208, a thermal path is created from lens 205, which is well known as one of the major heat sources for transducer face temperature, through side shield 206 and RFI shield 207 to cable shield 208. The thermal path draws heat away from lens 205 of the transducer assembly to lower the face temperature of the ultrasound probe to an acceptable level for use with humans. Reducing the transducer face temperature enables the transducer layer 202 to be operated at a higher transmit voltage/power to deliver more acoustic energy into the body, thereby improving ultrasound image quality.

In one embodiment, by coupling the thermal path formed by thermally conductive layer 204, side shield 206, and RFI shield 207 to cable shield 208, an enclosed shielded cage is created when all these components and coupling materials are also electrically conductive. In one embodiment, this enclosed shield cage is a Faraday cage, which in the case of the ultrasound transducer assembly is an enclosure used to block electromagnetic fields by causing the electric charges within the ultrasound transducer assembly to be distributed such that they cancel the field's effect in the interior of the ultrasound transducer assembly.

Figure 2B:
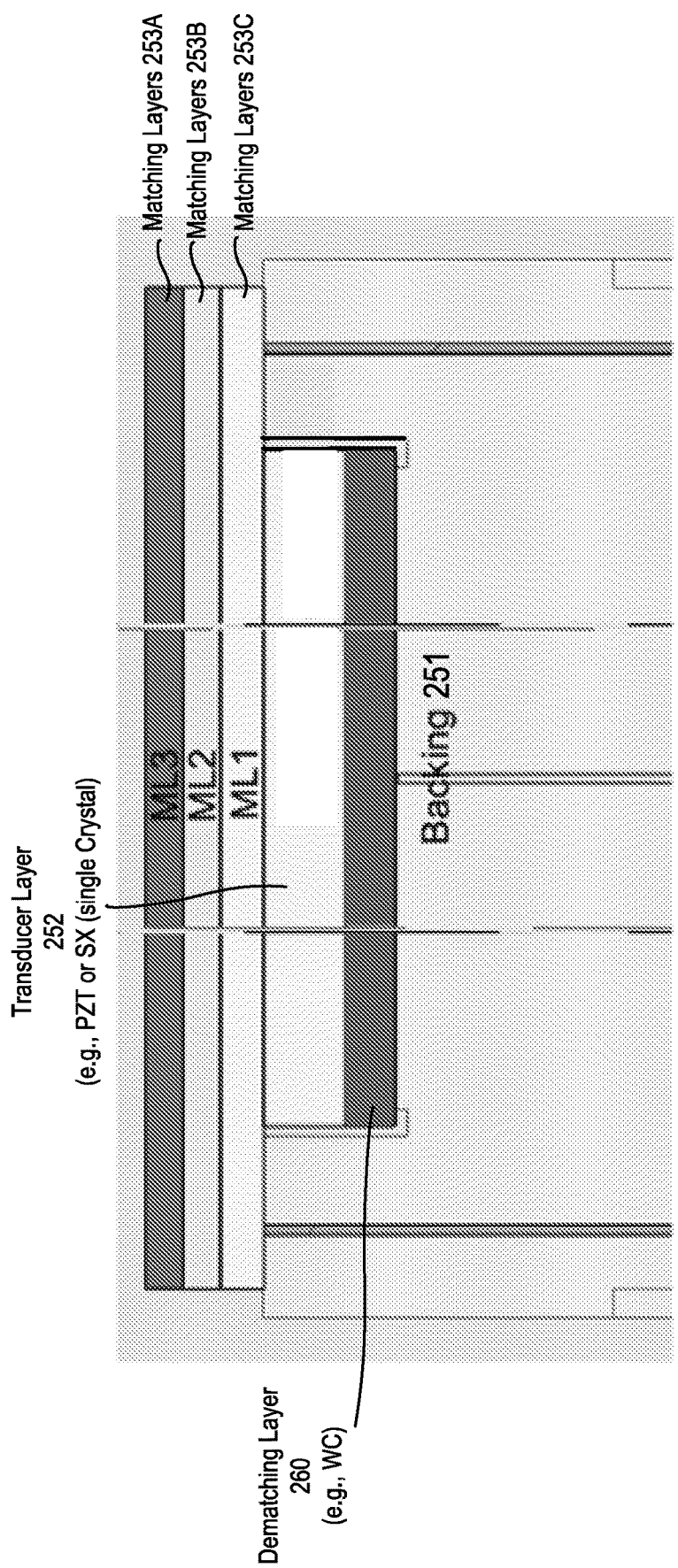
FIG. 2B illustrates a side section view of another embodiment of an ultrasound transducer array assembly.

FIG. 2B illustrates a side section view of another embodiment of an ultrasound transducer array assembly. Referring to FIG. 2B, a dematching layer 260 (e.g., tungsten carbide (WC), etc.) is attached to a transducer layer 252 (e.g., PZT, SX (single crystal), etc.) in a stack within the trough of backing block 251. In one embodiment, this transducer/dematching assembly is bonded together and is referred to herein as transducer/dematching coupon. When the transducer comprises PZT, the assembly is referred to herein as a PZT/dematching assembly, or a PZT/dematching coupon. In one embodiment, the PZT/dematching coupon is then stackbonded with all the front matching layers 253A-C and backing block 251. While only three matching layers are shown, any number of matching layers may be used (e.g., ML1, ML2, ML3, ML4, ML5, . . . ). Also, note that these layers may be attached to each other using techniques other than stackbonding.

In one embodiment, transducer layer 202 and one or more matching layers 203 may undergo a dicing operation in which a plurality of trenches, grooves or kerfs are diced into transducer layer 202 and matching layers 203. As those of ordinary skill in the art will appreciate, the kerfs can be configured to isolate individual elements of transducer layer 202 and/or attenuate acoustic crosstalk between the individual elements. The kerfs have not been shown in FIG. 2A to avoid obscuring the techniques disclosed herein.

In one embodiment, the kerfs are at least partially filled with filler. In one embodiment, the filler comprises one or more materials that fill at least a portion of the kerfs. In one embodiment, the filler comprises a composite material that includes microballoons suspended in an epoxy or a polymer. The microballoons can include glass or plastic microspheres surrounding or encapsulating a gas (e.g., air, a hydrocarbon gas, etc.) or be solid microspheres. The microballoons or microspheres can be mixed with an epoxy or polymer in varying ratios to achieve composite materials having varying consistencies and densities. In one embodiment, for example, a "slurry" composite material is mixed with microballoons and epoxy or a polymer. Such filler materials are well-known in the art.

The dicing and associated creation of the kerfs may occur after the thermally conductive layer has been overlaid onto the matching layers or before the thermally conductive layer has been overlaid onto the matching layers. The process depicting the different processes with timing for both of the array metalization operations is shown in the flow diagram of FIG. 4.

Figure 4:
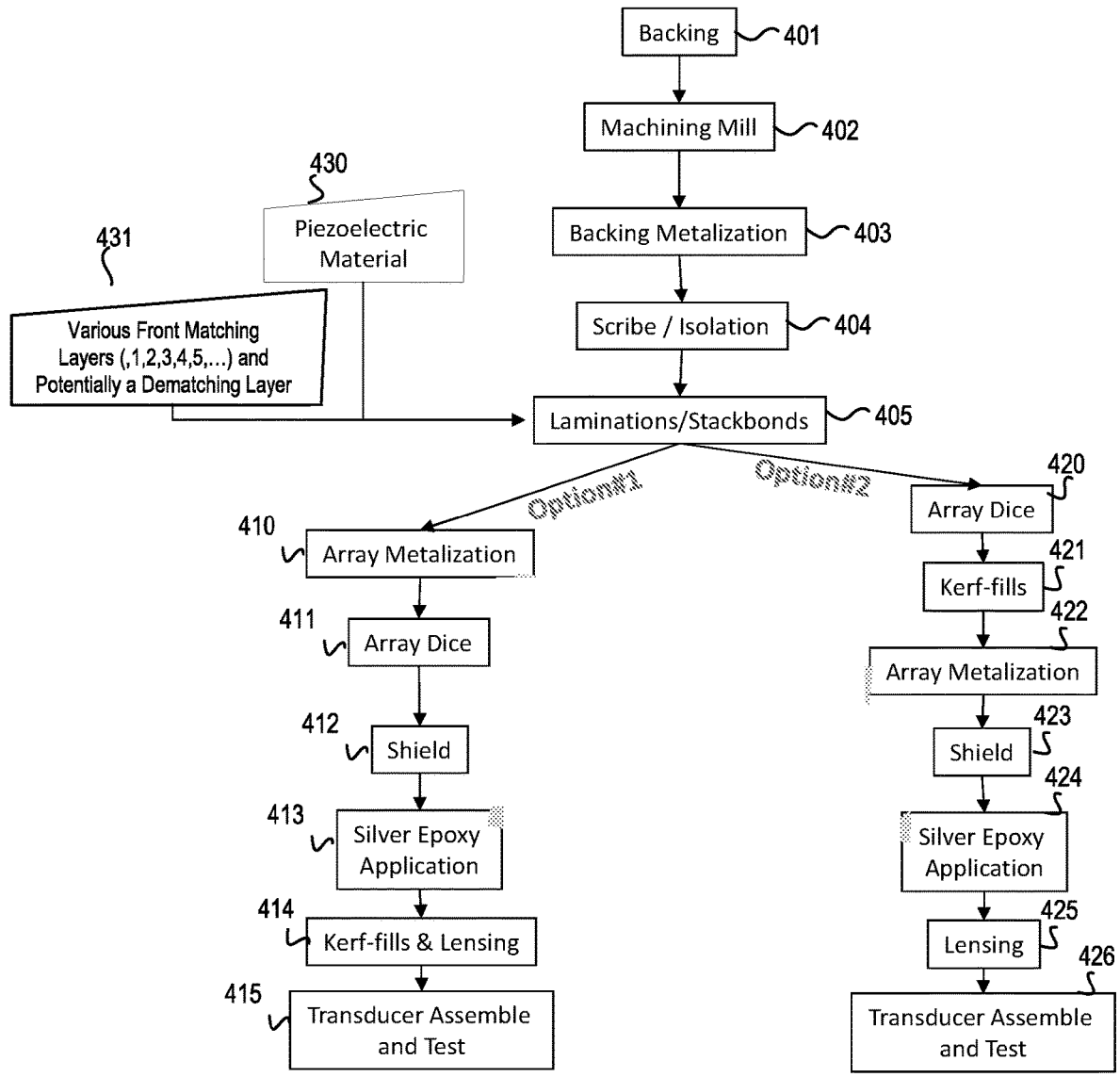
FIG. 4 is a flow diagram of one embodiment of a process of constructing an ultrasound transducer assembly.

Referring to FIG. 4, in one embodiment, a process of constructing an ultrasound transducer assembly in accordance with embodiments of the disclosed technology starts with casting a backing layer or backing block (process block 401) and performing a machining/milling process (process block 402) to produce a channel or trough in the backing layer 401. In one embodiment, backing layer 401 undergoes a backing metalization process (process block 403). Then scribe lines are made on backing layer 401 (block 404).

After scribe lines have been created, transducer layer 430 and various matching and dematching layers 431 are laminated/bonded together with the backing layer 401 into a stack (process block 405). This bonding is performed in a manner well-known in the art.

At this point, the process can proceed in two ways depending on whether dicing and associated creation of the kerfs occur after the thermally conductive layer has been overlaid onto matching layers 431 or before the thermally conductive layer has been overlaid onto matching layers 431.

At process block 410, a coating process is performed to apply the thermally conductive layer (e.g., thermally conductive layer 204 of FIG. 2A) onto the stack of transducer 430 and matching layers 431. In one embodiment, the coating process comprises a sputter or other vapor deposition process or another deposition process. In one embodiment, the deposition process doesn't impact acoustic performance of the ultrasound transducer.

Then, at process block 411, the process performs one or more cuts to form one or more kerfs in the transducer 430, matching layers 431 and the thermally conductive layer. Thereafter, at process block 412, the process attaches a side shield (e.g., side shield 206 of FIG. 2A) to the thermally conductive layer by applying an adhesive such as, for example, but not limited to, silver epoxy (process block 413).

At block 414, the process inserts or otherwise fills at least a portion of the kerfs formed during the array dice process (process block 411) with a filler material (e.g., RTV, microballoons, etc.) and applies a lens material (e.g., RTV or another suitable lens material) onto the front of the transducer assembly. The subsequent transducer assembly and test process (process block 415) includes, but is not limited to, attaching transducer to cable, applying an RFI shield (e.g., RFI shield 207 in FIG. 2A), applying an adhesive such as, for example, but not limited to, silver epoxy to connect the RFI shield to the side shield, and the RFI shield to the cable shield, and finally testing.

If the thermally conductive layer (e.g., thermally conductive layer 204 of FIG. 2A) is performed after kerf filling, process blocks 420-426 are performed. These process operations are the same as the operations performed in process blocks 410-415 except that the kerf fill and lensing processes are separated.

Figure 5:
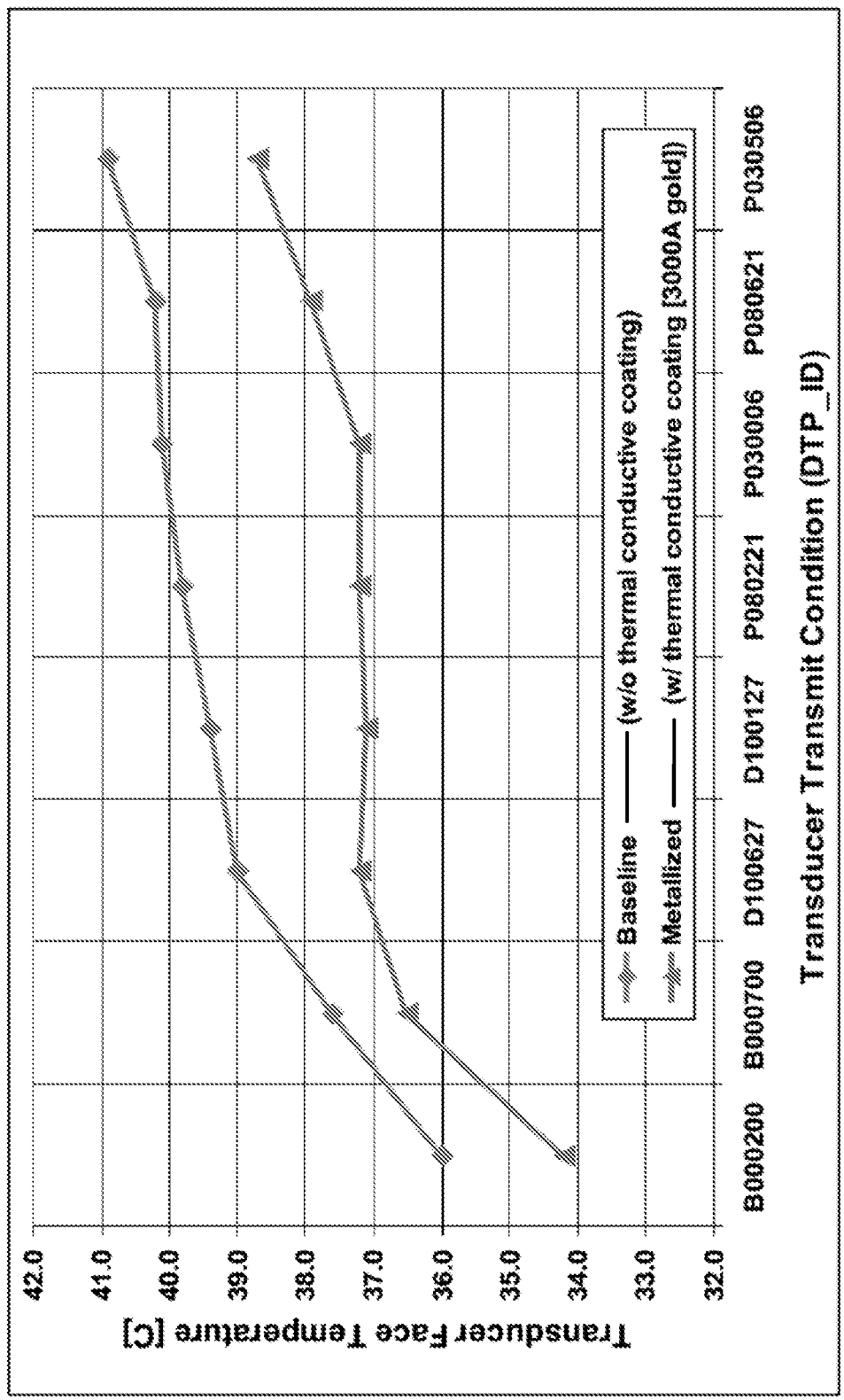
FIG. 5 is a table illustrating results of the use of the techniques described herein for reducing transducer face temperature.

FIG. 5 demonstrates the results of use of the techniques described herein for reducing transducer face temperature. These results were observed in some initial lab thermal measurements of a 9 MHz transducer face temperature. With respect to the transducer face temperature shown in FIG. 5 for a number of transducer imaging transmit conditions, the upper graph shows measurements from a transducer assembly without a thermally conductive layer, while the lower graph shows measurements from the same transducer assembly but with a thermally conductive layer.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. An ultrasound transducer assembly comprising:
a transducer layer configured to emit ultrasound energy;
one or more matching layers on the transducer layer;
a thermally conductive layer on the one or more matching layers;
a backing layer including a channel to hold the transducer layer and outer sides coupled to the channel, wherein the thermally conductive layer is wrapped around the outer sides of the backing layer and is separated from the transducer layer by the backing layer,
a first shield coupled to the thermally conductive layer at a first connection point on at least one of the outer sides of the backing layer, and a radio-interference (RFI) shield connected to the first shield at a second connection point on the at least one of the outer sides of the backing layer.

2. The ultrasound transducer assembly of claim 1 wherein the thermally conductive layer comprises a material with thermal conductivity greater or equal to 100 W/m·K.

3. The ultrasound transducer assembly of claim 1 wherein the thermally conductive layer comprises an electrically conductive material.

4. The ultrasound transducer assembly of claim 1, further comprising:
a lens on the thermally conductive layer.

5. The ultrasound transducer assembly of claim 1, wherein the thermally conductive layer comprises gold, copper, silver, aluminum, magnesium, beryllium, brass, bronze, molybdenum, rhodium, tungsten, zinc, carbon, and aluminum nitride.

6. The ultrasound transducer assembly of claim 1, further comprising:
a dematching layer under a bottom surface of the transducer layer in the channel in the backing layer.

7. The ultrasound transducer assembly of claim 1, wherein the thermally conductive layer is patterned with thermally conductive and electrically conductive materials.

8. The ultrasound transducer assembly of claim 1, wherein the thermally conductive layer comprises a thermally conductive layer on an electrically conductive layer.

9. The ultrasound transducer assembly of claim 1, wherein the thermally conductive layer is wrapped around the outer sides of the backing layer and is separated from the transducer layer by the backing layer to form an enclosed shielded cage.

10. The ultrasound transducer assembly of claim 1, wherein the thermally conductive layer comprises a 3000 Angstrom gold layer.

11. An ultrasound apparatus comprising:
a display screen;
an ultrasound imaging subsystem coupled to the display to generate ultrasound images on the display screen;
an ultrasound control subsystem coupled to control the imaging subsystem; and
an ultrasound transducer assembly comprising
a transducer layer configured to emit ultrasound energy,
one or more matching layers on the transducer layer,
a thermally conductive layer on the one or more matching layers, and
a backing layer including a channel to hold the transducer layer and outer sides coupled to the channel, wherein the thermally conductive layer is wrapped around the outer sides of the backing layer and is separated from the transducer layer by the backing layer;
a first shield coupled to the thermally conductive layer at a first connection point on at least one of the outer sides of the backing layer; and
a radio-interference (RFI) shield connected to the first shield at a second connection point on the at least one of the outer sides of the backing layer.

12. The ultrasound apparatus of claim 11 wherein the thermally conductive layer comprises a material with thermal conductivity greater or equal to 100 W/m·K.

13. The ultrasound apparatus of claim 11 wherein the thermally conductive layer comprises an electrically conductive material.

14. The ultrasound apparatus of claim 11 wherein the thermally conductive layer comprises gold, copper, silver, aluminum, magnesium, beryllium, brass, bronze, molybdenum, rhodium, tungsten, zinc, carbon, and aluminum nitride.

15. The ultrasound apparatus of claim 11 further comprising:
a dematching layer under a bottom surface of the transducer layer in the channel in the backing layer.

16. The ultrasound apparatus of claim 11, wherein the ultrasound transducer assembly further comprises:
a lens on the thermally conductive layer.

17. The ultrasound apparatus of claim 11, wherein the thermally conductive layer comprises a thermally conductive layer on an electrically conductive layer.

18. The ultrasound apparatus of claim 11, wherein the thermally conductive layer is wrapped around the outer sides of the backing layer and is separated from the transducer layer by the backing layer to form an enclosed shielded cage.

* * * * *